US008591392B2

(12) United States Patent
Bentwich et al.

(10) Patent No.: US 8,591,392 B2
(45) Date of Patent: Nov. 26, 2013

(54) METHOD AND SYSTEM FOR NEUROLOGICAL TREATMENT

(75) Inventors: Jonathan Bentwich, Ramat Yshai (IL); Eyal Baror, Shoham (IL); Samuel Faran, Holon (IL); Amir Katz, Haifa (IL)

(73) Assignee: Neuronix Ltd., Yoknea'm (IL)

( * ) Notice: Subject to any disclaimer, the term of this patent is extended or adjusted under 35 U.S.C. 154(b) by 249 days.

(21) Appl. No.: 12/994,553

(22) PCT Filed: Apr. 6, 2010

(86) PCT No.: PCT/IL2010/000289
§ 371 (c)(1),
(2), (4) Date: Jan. 24, 2011

(87) PCT Pub. No.: WO2010/113164
PCT Pub. Date: Oct. 7, 2010

(65) Prior Publication Data
US 2011/0118534 A1      May 19, 2011

Related U.S. Application Data

(60) Provisional application No. 61/166,628, filed on Apr. 3, 2009.

(51) Int. Cl.
*A61N 2/00* (2006.01)
(52) U.S. Cl.
USPC .............................................. 600/12; 607/45
(58) Field of Classification Search
USPC .......................................... 600/9–15; 607/45
See application file for complete search history.

(56) References Cited

U.S. PATENT DOCUMENTS

| 6,198,958 | B1 | 3/2001 | Ives et al. |
| 2004/0088024 | A1 | 5/2004 | Firlik et al. |
| 2004/0138578 | A1* | 7/2004 | Pineda et al. ................. 600/544 |
| 2006/0058853 | A1* | 3/2006 | Bentwich ........................ 607/45 |
| 2006/0287566 | A1* | 12/2006 | Zangen et al. .................. 600/15 |
| 2007/0088404 | A1 | 4/2007 | Wyler et al. |

FOREIGN PATENT DOCUMENTS

WO    2009/044271 A2    4/2009

OTHER PUBLICATIONS

International Search Report from corresponding International Application No. PCT/IL2010/000289 mailed Sep. 9, 2010.
Sitzer et al., "Cognitive Training in Alzheimer's Disease: A Meta-Analysis of the Literature", Acta Psychiatr Scand 2006: 114: pp. 75-90, Jan. 17, 2006.
Cotelli et al., "Improved Language Performance in Alzheimer Disease Following Brain Stimulation", J. Neurol Neurosurg Psychiatry (2010), pp. 1-4, Feb. 13, 2010.

(Continued)

*Primary Examiner* — Christine Matthews
*Assistant Examiner* — Laura Fajardo
(74) *Attorney, Agent, or Firm* — Browdy and Neimark, PLLC

(57) ABSTRACT

The present invention provides a system and method for neurological treatment. The system of the invention includes a neurological stimulation (NS) modality that delivers neurological stimulation to a first brain region and a cognitive training (CT) that delivers CT to a second brain region, where activation of the CT modality occurs at a predetermined time relative to the activation period of the NS modality. In one embodiment, the NS and CT are interlaced. The first and second brain regions may be the same brain regions or different brain regions. The invention may be used, for example, in the treatment of dementia, neurological conditions or psychiatric conditions.

17 Claims, 1 Drawing Sheet

(56) References Cited

OTHER PUBLICATIONS

Cotelli et al., "Effect of Transcranial Magnetic Stimulation on Action Naming in Patients with Alzheimer Disease", Arch Neurol/vol. 63, Nov. 2006, pp. 1602-1604.

Mottaghy et al., "Enhancing Picture Naming with Trascranial Magnetic Stimulation", Behavioral Neurology 17 (2006), pp. 177-186.

Cotelli et al., "Transcranial Magnetic Stimulation Improved Naming in Alzheimer Disease Patients at Different Stages of Cognitive Decline", European Journal of Neurology 2008, 15: pp. 1286-1292, May 7, 2008.

Mottaghy et al., "Facilitation of Picture Naming After Repetitive Transcranial Magnetic Stimulation", American Academy of Neurology, vol. 53(8), pp. 1806-1812, Nov. 10, 1999.

Hallett, "Transcranial Magnetic Stimulation and the Human Brain", Nature, vol. 406, pp. 147-150, Jul. 13, 2000.

Maeda et al., "Interindividual Variability of the Modulatory Effects of Repetitive Transcranial Magnetic Stimulation on Cortical Excitability", Exp Brain Res (2000) 133, pp. 425-430, Jun. 21, 2000.

Onder et al., "Reality Orientation Therapy Combined with Cholinesterase Inhibitors in Alzheimer's Disease: Randomised Controlled Trial", British Journal of Psychiatry (2005), 187, pp. 450-455, Jan. 28, 2005.

Orrell et al., "A Pilot Study Examining the Effectiveness of Maintenance Cognitive Stimulation Therapy (MCST) for People with Dementia", International Journal of Geriatric Psychiatry 2005; 20, pp. 446-451, Dec. 14, 2004.

Spector et al., "Efficacy of an Evidence-Based Cognitive Stimulation Therapy Programme for People with Dementia", British Journal of Psychiatry (2003), 183, pp. 248-254, May 13, 2003.

* cited by examiner

METHOD AND SYSTEM FOR NEUROLOGICAL TREATMENT

RELATED APPLICATIONS

This application is a national phase filing under 35 U.S.C. 371 of International Application No. PCT/IL2010/000289, filed on Apr. 6, 2010, and claims the benefit of U.S. Provisional Patent Application No. 61/166,628, filed Apr. 3, 2009, the entirety of these applications are hereby incorporated herein by reference for the teachings therein.

FIELD OF THE INVENTION

This invention relates to medical devices, and more specifically to such devices for treating neurological and or psychiatric disorders or conditions.

BACKGROUND OF THE INVENTION

The following prior art documents are considered to be relevant for an understanding of the invention.

Cotelli et al. Archives of Neurology 2006; 63: 1602-1604.
Cotelli et al. European Journal of Neurology 2008, 15: 1286-1292).
Hallett, Nature 2000; 406: 147-50.
Maeda et al., Exp Brain Res 2000; 133: 425-30.
Mottaghy et. al, Behavioral Neurology 17 (2006), 177-186.
Mottaghy et. al; Neurology 53(8) (10 Nov. 1999), 1806-1812.
Oder et al., *The British Journal of Psychiatry* (2005) 187: 450-455.
Orrelli et al., Int J Geriatr Psychiatry 2005; 20: 446-451.
Spector et al., *The British Journal of Psychiatry* (2003) 183: 248-254.
WO 2009/044271

Dementia is a serious loss of cognitive ability in a previously-unimpaired person, beyond what might be expected from normal aging. It may be static, the result of a unique global brain injury, or progressive, resulting in long-term decline due to damage or disease in the body. Although dementia is far more common in the geriatric population, it may occur in any stage of adulthood. Dementia which begins gradually and worsens progressively over several years is usually caused by neurodegenerative disease, that is, by conditions affecting only or primarily the neurons of the brain and causing gradual but irreversible loss of function of these cells.

Dementia is a non-specific illness syndrome in which affected areas of cognition may be memory, attention, language, and problem solving, as well as basic and instrumental activities of daily living (ADLs), social skills, and behavioral disturbances.

Especially in the later stages of the condition, affected persons may be disoriented in time (not knowing what day of the week, day of the month, or even what year it is), in place (not knowing where they are), and in person (not knowing who they are or others around them).

The causes of dementia depend on the age at which symptoms begin. In the elderly population (usually defined in this context as over 65 years of age), a large majority of cases of dementia are caused by Alzheimer's disease and vascular dementia. Dementia with Lewy bodies is another fairly common cause, which again may occur alongside either or both of the other causes. Hypothyroidism sometimes causes slowly progressive cognitive impairment as the main symptom, and this may be fully reversible with treatment. Normal pressure hydrocephalus, though relatively rare, is important to recognize since treatment may prevent progression and improve other symptoms of the condition. However, significant cognitive improvement is unusual.

Various types of brain injury, occurring as a single event, may cause irreversible but fixed cognitive impairment. Traumatic brain injury may cause generalized damage to the white matter of the brain, or more localized damage. A temporary reduction in the brain's supply of blood or oxygen may lead to hypoxic-ischemic injury. Strokes (ischemic stroke, or intracerebral, subarachnoid, subdural or extradural hemorrhage) or infections (meningitis and/or encephalitis) affecting the brain, prolonged epileptic seizures and acute hydrocephalus may also have long-term effects on cognition. Excessive alcohol use may cause either alcohol dementia or Korsakoffs psychosis (and certain other recreational drugs may cause substance-induced persisting dementia); once overuse ceases, the cognitive impairment is persistent but non-progressive.

Alzheimer's disease (AD), also called Alzheimer disease, senile dementia of the Alzheimer Type (SDAT) or simply Alzheimer's, is the most common form of dementia. It is an incurable, degenerative, and terminal disease and is generally diagnosed in people over 65 years of age, although the less-prevalent early-onset Alzheimer's can occur much earlier. In 2006, there were 26.6 million sufferers worldwide, with about ⅓ of people over the age of 80 suffering from it. Alzheimers is predicted to affect 1 in 85 people globally by 2050. Public expenditure on AD is overwhelming, reaches nearly 100 B$ per annum in the United States alone, and over 250 B$ per annum in the largest seven western countries.

Although the course of Alzheimer's disease is unique for every individual, there are many common symptoms. In the early stages, the most commonly recognised symptom is memory loss, such as difficulty in remembering recently learned facts. Diagnosis is usually confirmed with behavioural assessments and cognitive tests. sometimes followed by a brain scan. As the disease advances, symptoms include confusion, irritability and aggression, mood swings, language breakdown, long-term memory loss, and the general withdrawal of the sufferer as their senses decline. Gradually, bodily functions are lost, ultimately leading to death.

Currently used treatments offer only a minor symptomatic benefit; no treatments significantly delay (beyond 3-6 months) or halt the progression of the disease are as yet available. Mental stimulation, exercise, and a balanced diet have been suggested, as both a possible prevention and a sensible way of managing the disease. Most patients today receive drugs of the family choline-esterase-inhibitors (ChEI), which increase the concentration in the brain of acetyl-choline. However, any improvement caused by the drug lasts for no more than 3 months, and then the normal degradation of the patient resumes.

Transcranial magnetic stimulation (TMS) is a noninvasive method to excite neurons in the brain in which weak electric currents are induced in brain tissue by rapidly changing magnetic fields. With MRI-based neuro-navigation control, the precision of targeting the TMS can be determined to an accuracy of about a few millimeters. Typical treatment parameters are a magnetic field strength of about 2 teslas on the coil surface and 0.5 T in the cortex, and a current rise time (zero to peak) of about 50-150 microseconds. The wave form may be monophasic or biphasic. Brain activity is triggered with minimal discomfort, and the functionality of the circuitry and connectivity of the brain can be studied. Both high- (>5 Hz) and low- (≤1 Hz) frequency rTMS have been employed, with the former being believed to have mainly an excitatory net effect and the latter having mainly an inhibitory net effect.

In single or paired pulse TMS, the pulses causes neurons in the neocortex under the site of stimulation to depolarise and discharge an action potential. When used in the primary motor cortex of the brain, it may produce muscle activity referred to as a motor-evoked potential (MEP) which can be recorded by electromyography (EMG). When used on the occipital cortex, "phosphenes" (flashes of light) might be detected by the subject. In most other areas of the cortex, the participant does not consciously experience any effect, but his or her behaviour may be slightly altered (e.g. a slower or faster reaction time in a cognitive task), or changes in brain activity may be detected using positron emission tomography (PET), electroencephalogram (EEG), or MRI.

Effects resulting from a single pule or paired pulses do not outlast the period of stimulation. In repetitive TMS (rTMS), effects which last longer than the period of stimulation are produced. The repetition rate for rTMS may be below 1 Hz ("slow TMS") to above 1 Hz ("rapid-rate TMS"). rTMS can increase or decrease the excitability of corticospinal or corticocortical pathways depending on the intensity of stimulation, coil orientation and frequency of stimulation. The effects of rTMS on cognitive processing in conjunction with a specific brain region has been observed to persist about 30 seconds after termination of the rTMS in a study that tested TMS effects on picture naming. (Mottaghy et. al (2006), 1999), General effects of rTMS, however, can outlast the stimulation period for up to 1-2 h (Hallett, Maeda).

TMS has been used in cognitive psychology/neuroscience to demonstrate causality. A noninvasive mapping technique such as fMRI is used to determine what regions of the brain are activated when a subject performs a particular task. If activity in the associated region is suppressed ("knocked out") with TMS stimulation, and the subject then performs the task worse than before, this would indicated that the region is used in performing the task.

For example, a subject asked to memorize and repeat a stream of numbers would typically show activation in the prefrontal cortex (PFC) via fMRI, indicating the association of this brain region in short-term memory. If the PFC is interfered with TMS, the subject's ability to remember numbers typically declines indicating that the PFC is involved short-term memory.

rTMS is an established method for the treatment of depression. In addition, TMS and rTMS have been studied in the treatment of various conditions, such as amblyopia, amyotrophic lateral sclerosis, auditory hallucinations associated with schizoaffective disorders, chronic pain, dysphasia, dystonia, epilepsy, fibromyalgia, hemispatial neglect, major depression migraine, obsessive-compulsive disorder, parkinson's disease, phantom limb, stroke, nonfluent aphasia, and tinnitus. However, results, to-date, remain inconclusive.

In recent studies, Cotelli et al stimulated left or right dlPFCs during object and action naming in a group of Alzheimer's dementia (AD) patients. Action naming performance immediately following rTMS was temporarily improved in all subjects during high-frequency stimulation of both left and right dlPFC compared with sham stimulation (Cotelli et al. 2006; 2008). However, it should be noted that these results represent only an immediate and temporary improvement in a specific cognitive test, measured during the application of the stimulus.

Cognitive training refers to any nonpharmacological intervention designed to improve cognition, regardless of mechanism of action. Typically, cognitive training focuses on specific cognitive domains or cognitively mediated domains of functioning, such as basic and instrumental activities of daily living (ADLs), social skills, and behavioral disturbances. Cognitive training includes cognitive stimulation, memory rehabilitation, reality orientation, and neuropyschological rehabilitation. A recent meta-analysis of studies testing cognitive training for early-stage AD between 1980 and 2004 supports that cognitive training is effective. Specifically, medium effect sizes were observed for learning, memory, executive functioning, ADLs, general cognitive problems, depression, and self-rated general functioning (Sitzer, D. I. et al.).

International patent publication WO 2009/044271 discloses a system and method for treatment of medical conditions related to the central nervous system. A brain region is stimulated with electric or magnetic fields. A cognitive feature of the brain region is also stimulated.

SUMMARY OF THE INVENTION

The present invention is based on the novel and unexpected finding that a combination of neurological stimulation, such as rTMS, with cognitive training has a synergistic effect, so that treatment of various neurological disorders using both neurological stimulation and cognitive training can achieve results that are superior to the results achieved by either neurological stimulation or cognitive training alone. In particular, the inventors have found that improvement in cognitive abilities following a treatment combining neurological stimulation and cognitive training may persist longer than the improvement obtained using either one of neurological stimulation and cognitive training.

In its first aspect, the present invention thus provides a system and method for neurological treatment. The system of the invention comprises a neurological stimulation (NS) modality configured to deliver neurological stimulation to a brain region and a cognitive training (CT) modality configured to deliver cognitive training to the same brain region. A processor is configured to activate the neurological stimulation modality and the cognitive training modality to execute a treatment regime consisting of at least two applications of NS and two applications of CT. NS typically causes a quantifiable physiological stimulation effect in the brain region being treated that has an initial level at the termination of the NS where the level of the physiological effect decays over time. In one embodiment of the invention, the CT is delivered to the brain region while the level of the physiological effect caused by the NS is above a predetermined fraction of the initial level of the physiological effect. Without wishing to be bound by a particular theory, it is believed that physiological effect caused by the NS usually decays with time and that beneficial effects of CT are enhanced when the CT is administered when the level of NS is still significant. The effect is further enhanced by repeated cycles of NS and CT, where each application of CT occurs while a physiological effect of the NS is significant.

The neurological stimulation may be rTMS in which case, the CT would typically start immediately after termination of the rTMS, and will continue for about 10-120 seconds.

In other embodiments of the invention, the NS may be any one or more of TMS, DC current, AC current, tDCS, EST, magnetic field, electric field, RF radiation, Microwave radiation, IR radiation, Optical and UV radiation, any form of X-ray, Ultrasound or any other form of mechanical waves, or any combination of the above. The source for the NS may be noninvasive or invasive. The NS may be either stimulatory (e.g.—enhancing the brain activity in the targeted region), or may be suppressor (e.g.—suppressing the brain activity in the targeted region), all in accordance with the clinical goal.

The NS and/or CT may be directed towards any single or multiple brain loci in brain regions associated with, for example, Alzheimer's disease, dementia, mild cognitive impairment, memory loss, aging, ADHD, Parkinson's disease, depression, addiction, substance abuse, schizophrenia, bipolar disorder, memory enhancement, intelligence enhancement, concentration enhancement, well-being or mood enhancement, self-esteem enhancement, language capabilities, verbal skills, vocabulary skills, articulation skills, alertness, focus, relaxation, perceptual skills, thinking, analytical skills, executive functions, sleep enhancement, motor skills, coordination skills, spots skills, musical skills, interpersonal skills, social skills and affective skills.

Any one or more of the brain regions stimulated by the NS or CT may be, for example, a left prefrontal region, frontal lobe, cingulated gyms, nispheres, temporal lobe, a parietal lobe, occipital lobe, amygdale ion, cerebellum, hippocampus, anthreonal, Peabody, plaques, tangles, brain stem, dula, corpus collasum, subcortical region, cortex, gyrus, white matter, or gray matter.

The CT may be, for example, tasks specifically designed to improve retention of names of common objects, face-name associations, object-location associations, performance on a prospective memory task, reality orientation, implementation of various cognitively stimulating tasks as questioning/ memorizing current events, solving simple computerized crossword puzzles and labyrinth etc. The CT may be visual stimulation, audio stimulation, olfactory stimulation, tactile stimulation, spatial stimulation.

CT may be selected so to train the same brain region, or a different brain region, than the region that was activated by the NS. Table 1 provides examples of CT believed to be directed towards several specific brain regions Thus, in its first aspect, the present invention provides a system for neurological treatment comprising:
(a) a neurological stimulation (NS) modality configured to deliver neurological stimulation to a brain region;
(b) a cognitive training (CT) modality configured to deliver CT to a brain region;
(c) a processor configured to execute a neurological treatment session, the treatment session comprising:
(i) for i=1 to M, where M is a number of brain regions, for j=1 to N(i), where N(i) is a number of times a first brain region i is to be stimulated, and N(i) is at least 2;
(a) activating the NS modality for a predetermined amount of time $T_{ij}$; and
(b) activating the CT modality to deliver CT to a second brain region, the CT modality being activated at a predetermined time relative to the activation of the NS modality.

The system of the invention may be used, for example, in the treatment of any form of dementia or other age related diseases, in the treatment of any form of neurological conditions, or in the treatment of any form of psychiatric conditions. The first brain region may be the same as the second brain region, or the first and second brain regions may be different. The NS may be applied non-invasively or invasively.

The occurrence j of the activation of the NS modality on brain region i may comprise delivering an amount $P_{ij}$ of neurological stimulation to the brain region i, wherein the neurological stimulation $P_{ij}$ causes a predetermined physiological effect. The physiological effect may have an initial level that decays in time after termination of the NS activation. Occurrence j of the activation of the NS modality may occur when the level of the predetermined physiological effect caused by occurrence j−1 of the activation of the NS

TABLE 1

| Brain Region | Cognitive Training |
| --- | --- |
| Broca's area | Similar Sentences: The patient sees 2 similar sentences, and needs to decide whether theses sentences have the same or different meanings (meaning encoding) |
| Broca's area | Wrong order: The patient sees a sentence, in which the order of the words can be either meaningful or meaningless. |
| Wernicke's area | Words vs. pseudo words. The patients see a string of either meaningful letters or a meaningless string of letters, and needs to decide whether this string is a meaningful word or not (lexical decision). |
| Wernicke's area | Categories: the patient sees a picture of an object, and needs to decide to which family of objects then depicted object belongs. |
| Left Dorso Lateral Prefrontal cortex (DLPFC) | The patient sees one or more colored shapes on the screen. After a while the shapes disappear, and one shape of the same type appears on the screen in a certain location. The patient has to decide whether the color of this shape appeared on the first slide. Similarly, the shape may change its location, and the patient has to identify it. |
| Left DLPFC | Letter memorizing. The patient sees a letter on the screen. After a while, a slide appears with a second letter in a different location. After a while a slide appears with a letter and the patient has to decide whether it is the same letter and same location as at the first slide. |
| Left/Right DLPFC | Action naming: the patient sees on the screen a photo or drawing of a person involved in some activity and needs to name the activity this person involved in.<br>Object naming: the patient sees on the screen a photo or drawing of an object and needs to name the object. |
| Parietal Left or Right | Concentration search: the patient sees a number of shapes or letters on the screen. The shapes have various colors and are in different locations/orientations. The patient has to determine whether a certain shape appears on the screen. | modality is above a predetermined fraction of the initial level, for j=2, ... N(i). The physiological effect may be an effect that is quantifiable by anyone or more of fMRI, EEG, PET, SPECT, cognitive measures, EMG and MEP. $P_{ij}$ may be a minimal amount of NS producing the predetermined physiological effect.

$$\sum_{i=1}^{M} \sum_{j=1}^{N(i)} P_{ij}$$

may be less than a predetermined constant. The predetermined constant may be selected so that a predetermined side effect does not occur when $$\sum_{i=1}^{M} \sum_{j=1}^{N(i)} P_{ij}$$

is below the predetermined constant.

The NS modality may be configured to deliver NS from two or more sources of NS. The NS modality may be configured to deliver two or more types of NS stimulation The NS may include any one or more of, DC current, AC current, DC voltage, AC voltage, tDCS, EST, magnetic field, electric field, RF radiation, microwave radiation, infra-red radiation, optical radiation, ultra-violet radiation, X-radiation, ultrasound, and mechanical waves.

The CT may involve a task designed to improve retention of names of common objects, face-name associations, object-location associations, performance on a prospective memory task, reality orientation, questioning/memorizing current events, solving simple computerized crossword puzzles and labyrinth. The CT may be selected from visual stimulation, audio stimulation, olfactory stimulation, tactile stimulation, and spatial stimulation.

The NS may be TMS, and the TMS may be rTMS. The rTMS may have, for example, a frequency of from 0.5 Hz to 30. The rTMS may have, for example, a pulse time of 0.5 to 5 sec. The rTMS may have, for example, an rTMS strength in the range of 40% to 110% of a motor threshold.

The system CT modality may be activated within 15 seconds after termination of the activation of the NS modality. Two consecutive activations of the NS modality may occur from 5 sec to 120 sec apart.

In its second aspect, the invention provides a method for neurological treatment comprising:
(ii) for i=1 to M, where M is a number of brain regions, for j=1 to N(i), where N(i) is a number of times a first brain region i is to be stimulated, and N(i) is at least 2,
    (a) activating a neurological stimulation (NS) modality for a predetermined amount of time; and
    (b) activating a cognitive training (CT) modality to deliver CT to a second brain region i, the CT modality being activated at a predetermined time relative to the activation period of the NS modality.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
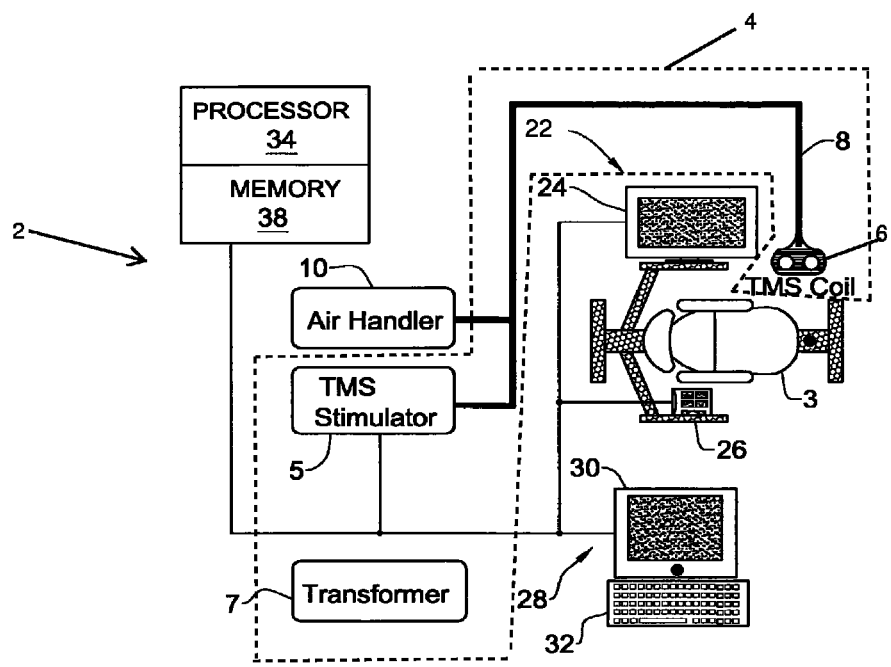
FIG. 1 shows a system for neurological training in accordance with one embodiment of the invention.

FIG. 1 shows a system 2 for neurological treatment in accordance with one embodiment of the invention. The system 2 includes a chair 3 to accommodate a subject undergoing neurological stimulation. The system 2 comprises a neurological stimulator, which in this embodiment, is a TMS modality 4 including TMS coil 6 that is connected to a TMS/rTMS controller 5 by means of a cable 8, and a medical grade transformer 7.

An air handler 10 provides cooling to the coil 6 by drawing air through the coil 6. In addition, the temperature of the coil is monitored during the therapy in order to keep its temperature within safe limits.

The system further comprises a CT modality 22 configured to deliver CT. For example, if the CT stimulation is visual stimulation, the CT device may include a display screen 24 and a subject input device such as a keyboard 26. The display screen 24 is disposed so as to be conveniently viewed by a subject in the chair 3, and the input device 26 is positioned so as to be conveniently accessible to the subject.

The TMS modality 4, the CT modality 22, are under the control of a processor 34. A user input terminal 28 includes a display screen 30 and a user input device such as a keyboard 32. The processor 34 includes a memory 38 for storing data relating to training protocols, data relating to the subject including MRI images, as well as storing data relating to training sessions. The processor 34 is configured to register the TMS coil 6 with a pre-acquired MRI image in order to deliver the TMS to a brain region indicated in the MM. The processor 34 is further configured to execute one or more predetermined treatment protocols, collect a subject's response to CT delivered during a training session, store the collected data in the memory, and to analyze the data.

A treatment session involves treating one or more brain regions. In accordance with this embodiment of the invention, for each brain region to be treated, the TMS modality is first activated to deliver rTMS to the brain region being treated where the parameters of the rTMS are selected so that the NS causes a predetermined physiological effect on at least the brain region being treated, where the physiological effect has an initial level that decays in time after termination of the NS. The CT modality is then activated to deliver CT to the brain region while the level of the NS is still above a predetermined fraction of the initial level. This cycle rTMS followed by CT may be repeated several times, to ensure the effectiveness of the treatment. The next episode of NS may be initiated sufficiently soon after the previous episode of NS, to ensure that the NS level does not decay below a predetermined fraction of the initial level during the treatment regime.

The physiological effect may be an effect quantifiable, for example, by fMRI.

Figure 2:
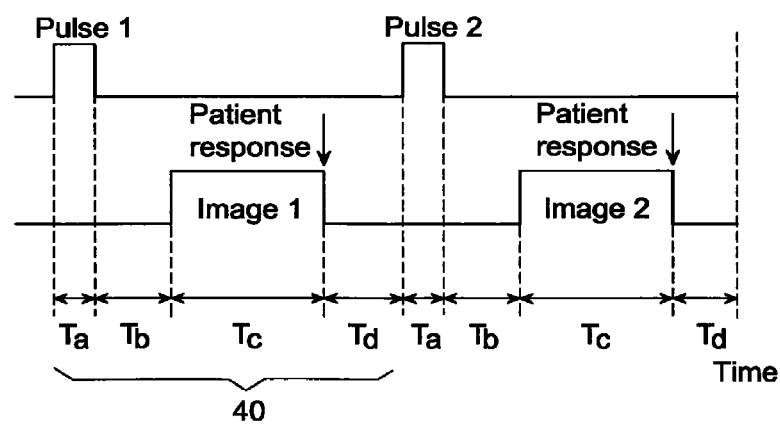
FIG. 2 shows a training session protocol in accordance with one embodiment of the invention.

FIG. 2 shows a typical treatment protocol for a first given brain region. The protocol commences with a first cycle 40 consisting of rTMS during a time period Ta, which may be for example, 0.1-10 sec, preferably 1-4 sec. followed by a first interlude of duration Tb (of duration, for example, between 0 to 10 sec) which is then followed by CT during a time period Tc (of duration, for example, between 5 to 300 secs, preferably 10-60 sec), and a second interlude of duration Td (between 0 to 10 sec). The time interval Tb+Tc+Td is selected to be sufficiently short that the level of the physiological effect is above a predetermined fraction of the initial level of the physiological effect that was present at the termination of the NS.

The frequency of the rTMS may be in the range of 0.1 Hz to 50 Hz, preferably 5-20 Hz, and the time between consecutive episodes of rTMS may be as indicated above. The first cycle 40 is then followed by at least one additional cycle 42 consisting of TMS, a first interlude, CT, and a second interlude. During each cycle, the CT is delivered while the brain region is in a primed state following the TMS. The protocol may involve control cycles in which no TMS is delivered (the coil 6 are not energized). The protocol of FIG. 2 may then be repeated for each of one or more additional brain regions.

EXAMPLE

In a clinical study performed in Israel, mild-moderate Alzheimer patients (DSM-IVR) (Mini Mental State Examination, MMSE from 18 to 24) were treated by the system of the invention in which the NS was BiPhasic rTMS with a frequency of 10 Hz, the pulse time was 2 sec, and the repetition rate was 30-50 sec. rTMS strength was set at 80-90% of the motor threshold. There were 6 brain regions which were treated in total, out of which 3 were treated on each day. Brain regions were chosen as those known to be affected and deteriorate in the AD. The brain regions treated were: Broca, Wemicki, Somatomotory Left, Somatomotory Right, Dorsolateral Prefrontal Right, Dorsolateral Prefrontal Left. The regions were located by an MRI scan. Each brain region received a dosage of 20 trains of pulses, or 400 pulses all together. The patient received a total of up to 1,200 pulses per day. CT started immediately or within 5 seconds following the end of the NS train, and lasted for 30-50 sec, until the next train of NS pulses wa administered. The cognitive performance of the patients was measured by ADAS-COG (Alzheimer Disease Assessment Score, Cognitive Sub Test), which is the standard test for evaluation of AD treatments (including, for example, drugs approved by FDA) at pre-treatment, between three to six days following the termination of 6 weeks of daily sessions, and between three to ten days following the termination of 3 months of twice-per-week treatment sessions. As a result of the treatment, patients' scores of the ADAS-COG improved by −4.2 points (after 6 weeks of treatment), and by another −4.0 points after the following 3 months of treatment (both statistically significant, p<0.05).

For comparison, CT by itself has been reported to provide an improvement of about −0.5 to −2 only. (See, for example: Spector et al., Orrelli et al., and Oder et al.)

For a treatment of TMS or rTMS alone, the inventors are unaware of any publication indicating improvement in cognitive functions beyond a transient effect observed only immediately following the treatment in AD patients (see, for example, Cotelli et al. 2008).

The invention claimed is:

1. A system for neurological treatment comprising:
   (a) a neurological stimulation (NS) modality configured to deliver neurological stimulation to a brain region;
   (b) a cognitive training (CT) modality configured to deliver CT to a brain region;
   (c) a processor configured to execute a neurological treatment session, the treatment session comprising:
      for i=1 to M, where M is a number of brain regions, and M is at least 1;
         for j=1 to N(i), where N(i) is a number of times a brain region i is to be stimulated, and N(i) is at least 2;
            (1) activating the NS modality on brain region i to provide an amount of neurological stimulation Pij selected as to cause a predetermined physiological effect; and
            (2) activating the CT modality to deliver CT to a brain region i, the CT modality being activated at a predetermined time relative to the activation period of the NS modality
   wherein, for j=2, . . . N(i), the occurrence j of the activation of the NS modality occurs when the level of the predetermined physiological effect, which has an initial level that decays in time after termination of the NS activation, caused by occurrence j−1 of the activation of the NS modality is above a predetermined fraction of the initial level.

2. The system according to claim 1, wherein the physiological effect is an effect that is quantifiable by any one or more of fMRI, EEG, PET, SPECT, ERP, cognitive measures, EMG and MEP.

3. The system according to claim 1, wherein Pij is the minimal amount of NS producing the predetermined physiological effect.

4. The system according to claim 1, wherein the NS is selected from the group consisting of at least one of, DC current, AC current, DC voltage, AC voltage, tDCS, EST, magnetic field, electric field, RF radiation, microwave radiation, infra-red radiation, optical radiation, ultra-violet radiation, X-radiation, ultrasound, and mechanical waves.

5. The system according to the claim 1, whereas the NS is applied invasively.

6. The system according to the claim 1, wherein the NS modality is configured to deliver one or both of (A) NS from two or more sources of NS and (B) two or more types of NS stimulation.

7. The system according to claim 1, wherein the CT involves a task designed to improve retention of names of common objects, face-name associations, object-location associations, performance on a prospective memory task, reality orientation, questioning/memorizing current events, or solving simple computerized crossword or labyrinth puzzles.

8. The system according to claim 1, wherein the CT is selected from the group consisting of visual stimulation, audio stimulation, olfactory stimulation, tactile stimulation, and spatial stimulation.

9. The system according to claim 1, wherein the NS is TMS.

10. The system according to claim 9, wherein the TMS is rTMS.

11. The system according to claim 10, wherein rTMS has a frequency of from 0.5 Hz to 30 Hz.

12. The system according to claim 10, wherein the rTMS has a pulse time of 0.5 sec to 5 sec.

13. The system according to claims 10, wherein the rTMS strength is in the range of 40% to 110% of a motor threshold.

14. The system according to claim 1, wherein the CT modality is activated within 15 seconds after termination of the activation of the NS modality.

15. The system according to claim 1, wherein two consecutive activations of the NS modality are from 5 sec to 120 sec apart.

16. The system according to the claim 1, whereas the NS is applied non-invasively.

17. A method for neurological treatment comprising:
   for i =1 to M, where M is a number of brain regions, and M is at least 1;

for j=1 to N(i), where N(i) is a number of times a brain region i is to be stimulated, and N(i) is at least 2,
- (1) activating a neurological stimulation (NS) modality on brain region i to provide an amount of neurological stimulation $P_{ij}$ selected as to cause a predetermined physiological effect; and
- (2) activating a cognitive training (CT) modality to deliver CT to brain region i, the CT modality being activated at a predetermined time relative to the activation of the NS modality wherein, for j=2, . . . N(i), the occurrence j of the activation of the NS modality occurs when the level of the predetermined physiological effect, which has an initial level that decays in time after termination of the NS activation, caused by occurrence j−1 of the activation of the NS modality is above a predetermined fraction of the initial level.

* * * * *